United States Patent [19]

Crytzer

[11] 4,360,774
[45] Nov. 23, 1982

[54] APPARATUS FOR MEASURING THE SURFACE INSULATION CHARACTERISTICS OF COATINGS ON MAGNETIC MATERIALS

[75] Inventor: Layton D. Crytzer, Natrona Heights, Pa.

[73] Assignee: Allegheny Ludlum Steel Corporation, Pittsburgh, Pa.

[21] Appl. No.: 137,868

[22] Filed: Apr. 7, 1980

[51] Int. Cl.$^3$ ............................................. G01R 31/16
[52] U.S. Cl. ...................................................... 324/54
[58] Field of Search ............ 324/54, 72.5, 149, 158 P, 324/158 F, 64, 65 P, 73 PC

[56] References Cited

U.S. PATENT DOCUMENTS

| | | | |
|---|---|---|---|
| 2,942,248 | 6/1960 | Huggins | 324/54 X |
| 3,458,807 | 7/1969 | Smith | 324/158 F |
| 4,156,841 | 5/1979 | Barnhart | 324/54 |
| 4,267,506 | 5/1981 | Shiell | 324/158 P |

OTHER PUBLICATIONS

Franklin, R. F., "Measurement and Control . . . of Laminated Magnetic Cores", ASTM Bulletin, Jan. 1947, pp. 57-61.
"Surface Insulation Resistivity of Single Strip Specimens", ASTM A717-75, pp. 182-185.

*Primary Examiner*—Gerard R. Strecker
*Attorney, Agent, or Firm*—Patrick J. Viccaro; Vincent G. Gioia

[57] ABSTRACT

An improved apparatus is disclosed for measuring the surface insulation characteristics of coatings on magnetic materials. This apparatus comprises an insulative button block having a plurality of protruding contact buttons stationarily mounted therein, with each contact button provided with a substantially flat contact surface, and with all contact surfaces lying substantially in the same plane. The apparatus further includes a press for urging the contact surfaces against the coated surface of the magnetic material, the electric circuitry necessary to apply a predetermined voltage potential between the contact surfaces and the magnetic material, and an ammeter to measure the current flow through the coating.

22 Claims, 4 Drawing Figures

APPARATUS FOR MEASURING THE SURFACE INSULATION CHARACTERISTICS OF COATINGS ON MAGNETIC MATERIALS

BACKGROUND OF THE INVENTION

The present invention pertains to an improved device for measuring the surface insulation characteristics of coatings on magnetic materials.

In January, 1947 R. F. Franklin's article entitled "Measurement and Control of Interlaminar Resistance of Laminated Magnetic Cores" appeared in the ASTM Bulletin. This article describes an instrument developed to test, under simulated operating conditions, insulating films applied to sheet steel to determine if such films are adequate. In recognition of its developer such instrument became well known as the Franklin tester.

Prior to the development of the Franklin tester the recognized method of testing the insulating value of interlaminar insulation was to apply insulating material to a number of small rectangular pieces of sheet steel. The sheets were stacked in a press and the electrical resistance between the top and bottom of the stack was measured.

The Franklin tester consists of a mounting block on which are assembled two parallel longitudinal rows of five vertically mounted steel rods free to move axially against surrounding spiral springs. At the end of each of the ten rods are brass insulated contact buttons. Each contact button is forced against the surface to be tested by the spring disposed about each cylindrical rod. In operation the Franklin tester is fastened to the head of a press. The bottom face of the contact buttons are urged against the coated surface of magnetic material to be tested at a predetermined pressure, and perhaps at a predetermined temperature, approximating the expected core pressures and temperatures to which the material will be exposed in service. The appropriate instrument circuitry is closed and the ammeter reading of between zero and 1.0 is recorded. A reading of 1.0 is indicative of poor surface film quality, while readings approaching zero indicate very good surface film quality.

The standard test method for "Surface Insulation Resistivity of Single-Strip Specimens" is set forth in ASTM Standard designation A717-75. In the described procedure the Franklin tester is attached to the head of a hydraulic press. Two drills are used to make electrical contact with the base metal to be tested. Polarity connections are made between the power supply and the Franklin tester to maintain the drills and the test specimen at a positive potential. A voltmeter is employed to indicate the voltage across the Franklin tester. The voltmeter load current appears as an error current and must be subtracted from the ammeter readings. The spring loaded, ten metallic contacts of fixed surface area are applied against one of the coated surfaces of the test specimen at a predetermined pressure. The effectiveness of the surface insulation is then indicated by a measurement of the average electrical current flowing between the contact buttons and the base metal.

Over the years, uniform contact pressure and uniform button contact area have been a source of concern to those using the Franklin tester. Such concern is evidenced by the various guidelines which have developed for the use of the Franklin tester including the following:

1. The head must be parallel to the test specimen.
2. All buttons should contact the test specimen simultaneously.
3. Springs must exert uniform pressure against all of the buttons as the head is applied against the test specimen.
4. All ten rods, or probes, must be perpendicular to the test specimen and remain perpendicular thereto as the buttons are compressed against the test specimen.
5. The buttons should not exhibit any lateral movement during a test.
6. The contact surface of all buttons should exert a uniform pressure throughout the entire contact area of each button as the buttons are urged against the test specimen.

It is generally recognized that faulty alignment of the probes can cause the contact buttons to wear unevenly, can result in the nonuniform application of spring urged pressure of the buttons against the test specimen, and can produce button skidding on the test specimen which could affect the electrical current reading. All of these conditions may distort the electrical resistivity measurements indicative of the quality of the insulative coating on the magnetic material being tested.

Also, the drill pressure and drill rotation may not be consistent from test to test with the Franklin tester. Such inconsistency is due primarily to the pressure differentials that may exist because the springs do not provide a uniform bias against all of the buttons. Thus, at light Franklin test pressures of about 200 to 300 psi, there is no assurance that the drill bits cut through the coating on the test sample to establish the requisite electrical contact with the base metal.

Efforts have been made to maximize the accuracy of the results obtained from the Franklin tester. For example, motor driven drill bits have been employed, various types of articulated buttons have been utilized, such as that recently disclosed in U.S. Pat. No. 4,156,841, the tolerance on the springs has been reduced, button surfaces have been machined and cleaned, and stainless steel buttons have replaced some brass buttons. Despite such efforts, an improved apparatus for more accurately and consistently measuring the surface insulation characteristics of coatings on magnetic materials is still desired. In particular, improvements in the Franklin tester are desired which would lead to improved confidence in the test results.

The present invention may be summarized as providing an improved apparatus for measuring the surface insulation characteristics of coatings on magnetic material. Such apparatus comprises an insulative button block having a plurality of protruding contact buttons stationarily mounted therein, with each contact button provided with a substantially flat contact surface and with all contact surfaces lying substantially in the same plane. The apparatus further includes a press for urging the contact surfaces against the coated surface of the magnetic material, the electric circuitry necessary to apply a predetermined voltage potential between the contact surfaces and the magnetic material, and an ammeter to measure the current flow through the coating.

Among the advantages of the present invention is the provision of an improved Franklin test apparatus which maximizes the accuracy of the results obtained by the replacement of the often troublesome spring biased probes, with non-depressable, or fixed probes.

An objective of the present invention is to provide an improved Franklin test apparatus which yields consistent, dependable and accurate results.

Another advantage of the improved apparatus of the present invention is that the improved apparatus is more readily and easily serviced than the conventional Franklin tester.

A further objective of this invention is to provide an apparatus which may follow the established and recognized ASTM procedure for testing insulation resistivity, yet will yield more dependable measurements thereof.

These and other objectives and advantages of the present invention will be more fully understood and appreciated with reference to following detailed description and the accompanying drawings.

DETAILED DESCRIPTION

Figure 1:
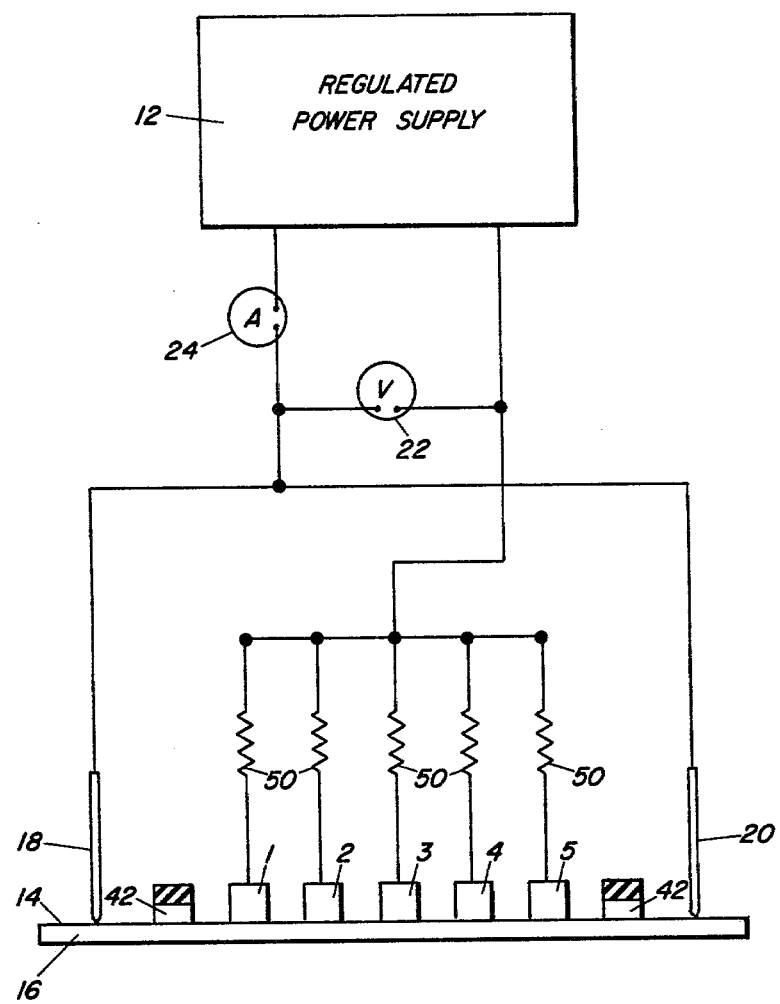
FIG. 1 is a schematic diagram of an apparatus of the present invention.

Referring particularly to the drawings, FIG. 1 shows a schematic diagram for an apparatus for measuring the surface insulation characteristics of coatings on magnetic material. As discussed above, such apparatus is commonly called a Franklin tester. The apparatus of the present invention schematically includes a regulated power supply 12 which supplies current at a constant voltage to ten contact buttons, five of which are shown in the schematic and are numbered 1–5. It should be understood that the regulated power supply 12 also supplies current at a constant voltage to the second row of five contact buttons 6–10 not illustrated in FIG. 1.

In the operation of the Franklin tester, all ten contact buttons are urged into contact with the coated surface 14 of the magnetic material 16 to be tested. Typically, the magnetic material is silicon steel strip material such as that used in the production of laminated cores for motors and transformers. The coatings provided on the magnetic material may include electrical insulative coatings such as enamel, varnish and oxide films.

Figure 2:
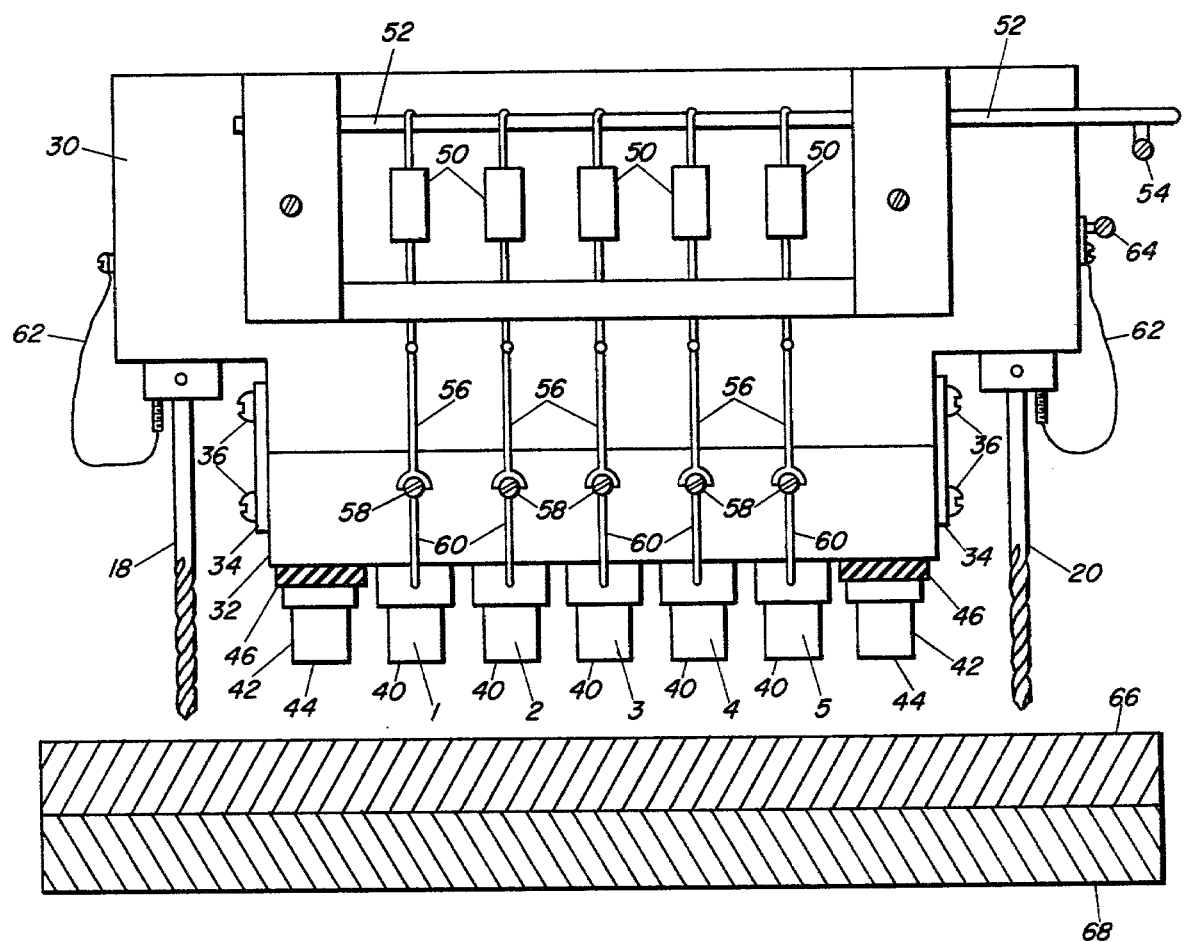
FIG. 2 is a side elevation view of an apparatus of the present invention.

Two drill bits 18 and 20, as shown in FIG. 2, typically located at each end of the Franklin tester are provided to pierce the insulative coating on the magnetic material 16. In the operation of the apparatus of the present invention any resulting current flow from the contact buttons which passes through the insulative coating returns to the power supply 12 through the electrically connected drill bits 18 and 20.

A voltmeter 22 is provided as shown to monitor and control the voltage, and an ammeter 24 is provided as shown to measure the magnitude of current which flows through the insulative coating on the test specimen 16.

FIG. 2 is a side elevation view of a Franklin test apparatus of the present invention. The illustrated apparatus includes a body block 30, typically made of a metallic material, such as carbon steel, and a button block 32 made of an insulating material, preferably a strong phenolic resin material. The button block 32 and body block 30 may be assembled with the use of mounting plates 34 and mounting screws 36 as illustrated in the drawing. It should be understood that any variety of mounting means may be employed including adhesives, clamping devices and the like.

Figure 3:
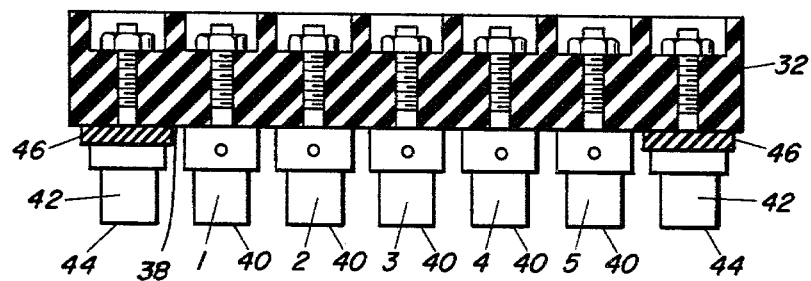
FIG. 3 is a side elevation view partially in cross-section of the button block of an apparatus of the present invention.

As best shown in FIG. 3, the ten contact buttons 1–10 are mounted in the button block 32. The buttons project only a short distance from the bottom surface 38 of the button block 32. Such distance of preferably less than about one and one-half inch, and more preferably less than about one inch, results in increased stability of the buttons which maintains the required parallelism and alignment in the apparatus. It should be noted that the contact probes of the conventional Franklin tester are about three inches in length to accommodate the spring biasing mechanism. The inherent instability of longer probes should be apparent, and certain associated disadvantages of the longer probes are discussed above. The present invention eliminates the prior art springs and considerably shortens the length of the contact probes which protrude from the apparatus.

Each of the ten contact buttons 1–10 is provided with a substantially flat contact surface 40, all of which lie substantially in the same plane. Preferably, the contact surfaces 40 lie in a plane parallel to the top and bottom surfaces of the body block 30 and the button block 32. As is conventional for conducting the Franklin test procedure in accordance with ASTM Standard A717-75, each contact surface 40 has a surface area of one-tenth square inch, thereby providing a total surface area of one square inch for each test.

Figure 4:
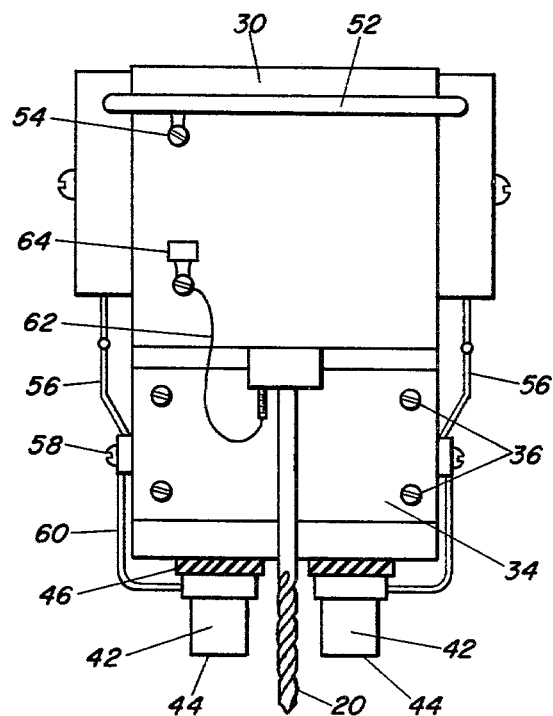
FIG. 4 is a front elevation view of the apparatus shown in FIG. 2.

The apparatus of the present invention is preferably provided with four wear buttons 42 which are provided with bottom contact surfaces 44. The wear buttons do not form a part of the measurement circuit and do not exert any significant amount of pressure on the material being tested. The wear buttons 42 are located and aligned at both ends of each row of contact buttons. The prime purpose of the wear buttons 42 is to protect the contact buttons from wear. The wear buttons 42 are resiliently mounted, such as with a rubber washer 46 as shown in FIGS. 3 and 4, in order that the wear buttons 42 retract as pressure is applied against the material being tested by the contact surfaces 40 of the stationary, non-depressable, fixed contact buttons 1–10.

As shown in the drawing, a resistor 50 is connected in series with each contact button to allow a total current of one ampere to flow when the insulation coating has zero resistance. The other end of each resistor 50 is connected to a common bus 52 which in turn is connected to the regulated power supply 12 at a wire terminal 54. In a preferred embodiment the resistor 50 is connected to the contact button through a tie wire 56, a screw terminal 58 and a button connector lead 60, which may be connected to the contact button by any conventional means such as a screw terminal, soldering or other means. By such assembly the button block 32 can be easily removed from the body block 30 by releasing the four mounting screws 36 and disconnecting the circuitry at the ten screw terminals 58. Such construction facilitates replacement of a minor portion of the apparatus as the need may arise. It should be understood by those skilled in the art that a number of button blocks 32 may be made available at the testing location for insertion into the Franklin tester as the then mounted button block 32 requires redressing and/or replacement.

The drill bits 18 and 20 on each end of the apparatus of the present invention preferably have their tips located below the plane wherein the button contact surfaces 40 lie. The drill bits 18 and 20 rotate when brought into contact with the material 16 to be tested. With such preferred structure, the problems associated with attaining sufficient drill penetration, particularly at light test pressures, are resolved since the drill bits 18 and 20 revolve the same amount regardless of the test pressure, due to the constant distance between the drill tips and the contact surfaces 40 during all tests. Rotation of the bits causes the tips of the bits to penetrate the insulation on the test material 16 and form a return path for the electric current from the test material 16 to the body block 30 through a flexible wire 62. From the body block 30 the current flows back to the regulated power supply 12 through a wire terminal 64 provided on the body block 30.

As is conventional for the Franklin tester, the body block 30 and button block 32 assembly and the associated circuitry is mounted as a unit in a pressure device such as a hydraulic press. Preferably a pressure plate 66, such as a smooth surfaced stainless steel plate, is provided opposite the contact surfaces 40 of the mounted assembly to support the material 16 to be tested. A cushion of resilient material 68 such as felt or rubber, may underlie the pressure plate 66 to accommodate minor deviations and bring the upper surface of the pressure plate 66 into substantially complete parallelism with the plane of the contact surfaces 40. In an alternative embodiment a cushion of resilient material may be inserted between the assembled body block 30 and button block 32 to accomplish such substantially complete parallelism.

The performance of the Franklin tester of the present invention having nondepressable, fixed buttons is considered to be an improvement over the conventional tester having spring biased contact probes. Such improved performance has been observed by applying the Franklin test against a sheet of paper with carbon paper disposed therebetween. The pressure of the contact surfaces 40 against the carbon paper acts to impose ten round "footprints" onto the test paper. The size, shape and shade of the ten footprints formed by this procedure with a Franklin tester of the present invention, are considerably more uniform than those of the ten footprints formed by this same procedure with a conventional spring loaded Franklin tester. Such improvements are noted even after moderate use of the tester, and even when compared to conventional testers which have redressed contact surfaces or articulated buttons. The uniformity in size, shape and shade of the footprints correlates to uniformity in electrical contact during the Franklin test procedure. Therefore, the apparatus of the present invention is considered to provide more accurate, reliable and readily comparable Franklin test results.

Whereas, the preferred embodiments of the present invention have been described above for the purpose of illustration it should be understood that various modifications of the details of this invention may be made without departing from the scope of this invention.

I claim:

1. An apparatus for measuring the surface insulation characteristics of coatings on magnetic material comprising:
   an insulative button block having a plurality of protruding electrically conductive contact buttons stationarily mounted therein, with each contact button provided with a substantially flat contact surface, and with the contact surfaces lying substantially in the same plane,
   means for pressing the entire button contact surfaces against the coated surface of the magnetic material, said means applies a uniform contact pressure over the entire button surface area and restrains lateral movement of the contact buttons,
   means for applying a voltage potential between the contact surfaces and the magnetic material, and
   means for measuring the current flow through the coating on the magnetic material to determine the surface insulation characteristics of said coating.

2. An apparatus as set forth in claim 1 wherein the button block is made of a phenolic resin.

3. An apparatus as set forth in claim 1 wherein there are ten contact buttons arranged in two, substantially aligned longitudinal rows of five contact buttons.

4. An apparatus as set forth in claim 3 wherein the contact surface of each contact button has an area of one-tenth square inch.

5. An apparatus as set forth in claim 1 wherein the contact buttons are brass.

6. An apparatus as set forth in claim 1 wherein the contact buttons are stainless steel.

7. An apparatus as set forth in claim 1 wherein the current flow through the coating on the magnetic material returns to the measuring means through at least one drill bit adapted to penetrate the coating and establish electrical contact with the magnetic material.

8. An apparatus as set forth in claim 7 wherein the tip of the drill bit lies below the plane in which the contact surfaces lie.

9. An apparatus as set forth in claim 7 wherein the longitudinal axis of the drill bit is substantially parallel to the longitudinal axes of the contact buttons.

10. An apparatus as set forth in claim 8 wherein the longitudinal axis of the drill bit and the longitudinal axes of the contact buttons are substantially perpendicular to upper and lower surfaces of the button block.

11. An apparatus as set forth in claim 1 wherein the contact buttons protrude less than about one and one-half inch from the bottom surface of the button block.

12. An apparatus as set forth in claim 1 wherein the contact buttons protrude less than about one inch from the button surface of the button block.

13. An apparatus as set forth in claim 1 further including wear buttons, resiliently mounted on the button block and protruding therefrom for a length at least equal to the length which the contact buttons protrude therefrom.

14. An apparatus as set forth in claim 13 wherein the wear buttons are provided with substantially planar bottom surfaces.

15. An apparatus as set forth in claim 13 wherein the resilient mounting of the wear buttons on the button block is provided by an elastic washer disposed between the wear button and the button block.

16. An apparatus as set forth in claim 1 wherein the button block is mounted to a separate metallic body block.

17. An apparatus as set forth in claim 16 wherein the mounting comprises a pair of mounting plates one end of each plate being fastened to the body block and the other end of each plate being fastened to the button block.

18. An apparatus as set forth in claim 1 further including a support plate disposed opposite the contact surfaces on which the magnetic material is supported.

19. An apparatus as set forth in claim 18 wherein the support plate is disposed on a resilient pad.

20. An apparatus as set forth in claim 19 wherein the pad is felt.

21. An apparatus as set forth in claim 19 wherein the pad is rubber.

22. An apparatus as set forth in claim 16 wherein a resilient pad is disposed between the body block and the button block.

* * * * *

UNITED STATES PATENT OFFICE
CERTIFICATE OF CORRECTION

Patent No. 4,360,774                 Dated November 23, 1982

Inventor(s) Layton D. Crytzer

It is certified that error appears in the above-identified patent and that said Letters Patent are hereby corrected as shown below:

In claim 12, line 3, cancel "button", first occurrence, and insert -- bottom --.

Signed and Sealed this

Twenty-ninth Day of March 1983

[SEAL]

Attest:

GERALD J. MOSSINGHOFF

Attesting Officer    Commissioner of Patents and Trademarks